(12) United States Patent
Miljak (10) Patent No.: US 10,416,248 B2
(45) Date of Patent: Sep. 17, 2019

(54) ON-LINE MAGNETIC RESONANCE MEASUREMENT OF CONVEYED MATERIAL

(71) Applicant: COMMONWEALTH SCIENTIFIC AND INDUSTRIAL RESEARCH ORGANISATION, Acton, Australian Capital Territory (AU)

(72) Inventor: David Geoffrey Miljak, New South Wales (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 0 days.

(21) Appl. No.: 15/754,461

(22) PCT Filed: Aug. 24, 2016

(86) PCT No.: PCT/AU2016/050778
§ 371 (c)(1),
(2) Date: Feb. 22, 2018

(87) PCT Pub. No.: WO2017/031537
PCT Pub. Date: Mar. 2, 2017

(65) Prior Publication Data
US 2018/0238976 A1 Aug. 23, 2018

(30) Foreign Application Priority Data
Aug. 24, 2015 (AU) ................................ 2015903415

(51) Int. Cl.
*G01R 33/36* (2006.01)
*G01N 24/08* (2006.01)
(Continued)

(52) U.S. Cl.
CPC .......... *G01R 33/3628* (2013.01); *G01G 9/00* (2013.01); *G01N 24/081* (2013.01);
(Continued)

(58) Field of Classification Search
CPC ............ G01R 33/3628; G01R 33/3642; G01R 33/307; G01R 33/3607; G01G 9/00; G01N 24/081; G01V 3/14
See application file for complete search history.

(56) References Cited

U.S. PATENT DOCUMENTS 8,710,837 B2 * 4/2014 Zank ....................... G01V 3/14
324/307
9,052,371 B1 * 6/2015 Apostolos ............ G01R 33/441
(Continued)

FOREIGN PATENT DOCUMENTS

| CN | 103809206 | 2/2013 |
|---|---|---|
| CN | 103338696 | 2/2014 |

(Continued)

OTHER PUBLICATIONS

Bennett, et al."On-Line Measurement of Mineralogy for OreSorting and Characterisation", In Applied Mineralogy:Developments in Science and Technology, ed Pecchio et al. (2004).
(Continued)

*Primary Examiner* — G. M. A Hyder
(74) *Attorney, Agent, or Firm* — Cooper & Dunham LLP (57) ABSTRACT

Magnetic resonance (MR) apparatuses, systems and methods for analysing a material. The magnetic resonance apparatuses include a primary loop defining an aperture that the material being analysed can pass through where the primary loop includes at least one pair of electrically conductive segments. The magnetic resonance apparatus also includes a pair of capacitance units corresponding to each pair of electrically conductive segments. Each capacitance unit is (Continued)

conductively connected to two adjoining conductive segments in series so that the primary loop forms a circuit for a radio frequency (RF) current. The primary loop is adapted to: conduct the RF electrical current so that the RF electrical current is predominantly in-phase over the entire primary loop. The magnetic resonance apparatus further includes: a pair of secondary coils corresponding to each pair of capacitor units, electrically conductively isolated from the primary loop. Each secondary coil is oriented to be magnetically coupled to the primary loop such that each secondary coil is capable of exciting RF voltages in the primary loop that are predominantly in-phase with each of the RF voltages excited by the other secondary coils. The magnetic resonance apparatus also includes a primary shield encompassing the primary loop and secondary coils for shielding electromagnetic radiation, the primary shield adapted to allow the material to pass through the aperture defined by the primary loop unobstructed.

20 Claims, 6 Drawing Sheets

(51) Int. Cl.
 G01V 3/14 (2006.01)
 G01R 33/30 (2006.01)
 G01G 9/00 (2006.01)
(52) U.S. Cl.
 CPC ....... *G01R 33/307* (2013.01); *G01R 33/3607* (2013.01); *G01R 33/3642* (2013.01); *G01V 3/14* (2013.01)

(56) References Cited

U.S. PATENT DOCUMENTS

| | | | |
|---|---|---|---|
| 9,476,953 B1* | 10/2016 | Zank | G01N 24/084 |
| 2005/0104593 A1 | 5/2005 | Laubacher | |
| 2005/0128069 A1* | 6/2005 | Skatter | G01V 5/0008 |
| | | | 340/522 |
| 2006/0122484 A1* | 6/2006 | Itozaki | G01R 33/441 |
| | | | 600/409 |
| 2008/0036462 A1 | 2/2008 | Schiano | |
| 2009/0096456 A1 | 4/2009 | Biber et al. | |
| 2011/0187363 A1* | 8/2011 | Zank | G01N 24/084 |
| | | | 324/307 |
| 2012/0242340 A1 | 9/2012 | Miljak | |
| 2014/0266196 A1* | 9/2014 | Dai | G01N 24/08 |
| | | | 324/309 |

FOREIGN PATENT DOCUMENTS

| | | |
|---|---|---|
| CN | 103582990 | 5/2014 |
| JP | 2014197935 | 10/2014 |
| WO | WO2011/066600 | 6/2011 |

OTHER PUBLICATIONS

Kruukka, et al. "Kiruna mineral processing starts underground—Bulk sorting by LIF." CIM Bulletin 95(1066): 79-84 (2002).
Bennett, et al. "Quantitative Measurement of Copper Mineralogy Using Magnetic Resonance", Mineral Engineering, V20, pp. 1344-1350 (2007).
Bennett, et al. "The measurement of chalcopyrite in rocks and slurries using magnetic resonance" , Mineral Engineering, V22, pp. 821-825 (2009).
Shultz, et al. "Quantitative aspects of nuclear quadrupole Resonance spectrometry of inorganics and minerals",Analytical Chemistry, V41 (4) p. 661 (1969).
Shultz, et al., "Applications of Nuclear Quadrupole Resonance Spectrometry to Analytical Chemistry", Applied Spectroscopy, V25 (3) p. 293 (1971).
Karr Jr, et al. "Wide-line nuclear magnetic resonance spectroscopy of sulphur-33 in minerals", Spectroscopy Letters, V1 (5) p. 205 (1968).
Abdullin, et al. "Investigation of copperminerals by NQR: crystallochemistly, electronic structure, lattice dynamics", Phys Chem Min., V14 p. 258 (1987).
Written Opinion and International Search Report issued in connection with International Application No. PCT/AU2016/050778, dated Oct. 26, 2016.
Extended European Search Report issued in connection with European Patent Application No. 16838122.6, dated Apr. 2, 2019.
Van Hecke et.al "Double tuned resonator designs from NMR spectroscopy" Journal of Magnetic Resonance, vol. 84, No. 1, Aug. 1, 1989, pp. 170-176.
Yoda K et.al "Inductive coupling to the slotted-tube quadrature probe", Journal of Magnetic Resonance, vol. 81, No. 2, Feb. 1, 1989, pp. 284-287.
Lehmann-Horn "rapid detection of arsenic minerals using portable broadband NQR: Broadband NQR Arsenic Detection", The 3rd EAA European Congress on Acoustics vol. 41, No. 19, Aug. 28, 2014, pp. 6765-6771.
Translation of Office Action issued by the China National Intellectual Property Administration in connection with Chinese Application No. 201680049268.1, dated Apr. 25, 2019.

\* cited by examiner

ON-LINE MAGNETIC RESONANCE MEASUREMENT OF CONVEYED MATERIAL

CROSS REFERENCE TO RELATED APPLICATIONS

This application is a § 371 national stage of PCT International Application No. PCT/AU2016/050778, filed Aug. 24, 2016, claiming priority of Australian Patent Application 2015903415, filed Aug. 24, 2015, the contents of each of which are incorporated herein by reference in their entireties.

TECHNICAL FIELD

The present invention generally relates to systems, methods and equipment for magnetic resonance measurement of bulk materials. More specifically, the present invention relates to magnetic resonance measurements of a continuous flow of bulk ore on conveyor systems.

BACKGROUND

Conveyor systems comprising conveyors, associated chutes and ore transfer stations are commonly used to convey large tonnages of ore in mining and mineral processing applications in order to transfer ore between mining and rock crushing stages, stockpiles or other unit processes. The open conveyor system geometry provides an opportunity to measure characteristics of the conveyed ore as it is being conveyed prior to downstream processing stages. For example, it may be desirable to measure the grade of specific elements or minerals in the ore with such on-line measurements.

The on-line measurement of ore grade may be used in a number of different ways to benefit mining. In sensor based bulk ore sorting, rapid detection of selected minerals or elements may be used to determine the economic value of consecutive ore parcels as they pass a sensor in a continuous stream. This information can be used to operate diverter or flop gates placed downstream of the sensor to sort the ore parcels into different stockpiles or channels. The resulting low grade ore streams may be diverted away from the relatively expensive comminution process, leading to potentially significant improvements in productivity. Bulk ore sorting can be applied to mining operations to lift productivity. Besides bulk ore sorting applications, sensors on conveyor systems may be used to determine longer term ore grades or rock-type trends.

Typically, benefit from sensing is maximised if the sensors are used in an on-line configuration, such that measurement information can be relayed to downstream processing plant in real-time, or at least in near real-time, such that a plant operator can act on the measurement information, within critical periods defined by either process residence or delay times.

However, there are few sensors suitable for bulk ore sorting as the ore sorting sensor ideally has a large sensing volume, and be able to measure ore on conveyors that contain long metallic cores. The sensor ideally can measure a significant fraction of the mineral stream very rapidly, and also enable quantitative measurements to be made. The sensor should also be able to measure groups of piled rocks in the conveyed ore stream.

It would therefore be of benefit to the mining industry if rapid sensors compatible with on-line measurement of materials on ore conveyor systems were developed.

Any discussion of documents, acts, materials, devices, articles or the like which has been included in the present specification is not to be taken as an admission that any or all of these matters: form part of the prior art base; were common general knowledge in the field relevant to the present disclosure as it existed before the priority date of each claim of this application; or could have been understood, regarded as relevant or reasonably expected to have been combined by a person skilled in the art.

SUMMARY

In a first aspect of the present invention, there is provided a magnetic resonance (MR) apparatus for analysing a material. The magnetic resonance apparatus includes a primary loop defining an aperture that the material being analysed can pass through where the primary loop includes at least one pair of electrically conductive segments. The magnetic resonance apparatus also includes a pair of capacitance units corresponding to each pair of electrically conductive segments. Each capacitance unit is conductively connected to two adjoining conductive segments in series so that the primary loop forms a circuit for a radio frequency (RF) current. The primary loop is adapted to: have a series resonance frequency suitable for magnetic resonance measurements of the target nuclei, conduct the RF electrical current so that the RF electrical current is predominantly in-phase over the entire primary loop, conduct the RF current to generate an RF magnetic field suitable for changing the magnetisation of the target nuclei, and have an RF signal current excited in the primary loop by precession of the magnetisation of the target nuclei. The magnetic resonance apparatus further includes: a pair of secondary coils corresponding to each pair of capacitor units, electrically conductively isolated from the primary loop. Each secondary coil is adapted to receive an RF excitation voltage from an RF transceiver via an electrical network, and is oriented to be magnetically coupled to the primary loop such that each secondary coil is capable of: exciting RF voltages in the primary loop that are predominantly in-phase with each of the RF voltages excited by the other secondary coils; and when the RF signal current is excited in the primary loop, having a corresponding RF current excited in the secondary coil to produce an RF output signal in the electrical network. The magnetic resonance apparatus also includes a primary shield encompassing the primary loop and secondary coils for shielding electromagnetic radiation, the primary shield adapted to allow the material to pass through the aperture defined by the primary loop unobstructed.

In some embodiments, the primary loop is a single turn loop. In some embodiments, the electrically conductive segments may include either: a single conductive ribbon; or a plurality of conductive elements electrically connected to each other in parallel.

In some embodiments, the capacitance of each capacitor unit is substantially equal to each other to facilitate the production of the RF electrical currents that are predominantly in-phase over the entire primary loop. The capacitance of each capacitor unit may be capable of being varied.

In some embodiments, the length of each of the electrically conductive segments is substantially equal to each other to facilitate the production of the RF electrical currents that are predominantly in-phase over the entire primary loop.

In some embodiments, the primary shield is connected to a reference voltage and one side of the secondary coil electrical network port is electrically conductively connected to the primary shield.

In some embodiments, the aperture is adapted to allow either a conveyor belt or a chute carrying the material being analysed to pass through.

In some embodiments, the magnetic resonance apparatus further includes at least one secondary shield located adjacent the primary shield, the secondary shield reducing the effect of spurious electromagnetic fields on the primary loop. The secondary shield may be a waveguide configured such that the material can pass through the secondary shield.

In some embodiments, the magnetic resonance apparatus further includes an RF transceiver. The RF transceiver includes an RF generator and is configured to produce the RF excitation voltages received by the electrical networks of at least two secondary coils.

In some embodiments, the magnetic resonance apparatus further includes an electrical coupling network where the electrical coupling network is connected to the two or more secondary coils and the RF transceiver and the electrical coupling network is configured to transmit RF electrical currents, produced by the RF transceiver, to the secondary coils such that predominantly in-phase RF excitation voltages can be produced in the primary loop.

In some embodiments, the magnetic resonance apparatus may further include a sampling circuit, wherein at least one of the conductive segments is adapted to enable a voltage at a location midway along the at least one conductive segment to be sampled, and the voltage sampled from the conductive segment is converted to a suitable voltage by the sampling circuit and input into the RF transceiver to at least partially compensate for electromagnetic noise.

In some embodiments, the magnetic resonance apparatus further includes two or more electrically floating electrode shields, each floating electrode shield corresponding to one conductive segment and located such that the corresponding conductive segment is located between the floating electrode shield and the primary shield.

In some embodiments, the magnetic resonance apparatus further includes one or more pilot coils magnetically coupled to the primary loop and adapted to produce an RF magnetic field at predetermined frequencies. The pilot coils may produce the RF magnetic field to thereby correct for changes in the transfer function.

In some embodiments, the magnetic resonance apparatus further includes one or more auxiliary coils magnetically coupled to the primary loop, the one or more auxiliary coils each having a termination, wherein the auxiliary coil alters the complex series impedance of the primary loop. The impedance of the termination for each auxiliary coil may be adjustable with an auxiliary control unit.

In a second aspect of the present invention, there is provided a magnetic resonance system for analysing a material. The system includes: the MR apparatus for analysing the material according to the first aspect; and a radio frequency (RF) transceiver including an RF generator and a transmit-receive switch. The RF transceiver is connected to the secondary coils and adapted to: apply an RF pulse sequence to the secondary coils with at least an operating frequency set to a predetermined frequency capable of inducing change in the magnetisation in an ensemble of target nuclei in the material, and receive an RF output signal generated by the secondary coils in cooperation with the transmit-receive switch.

In a third aspect of the present invention, there is provided a method of determining the mass of a target material in an ore. The method includes: passing a material through an aperture of a primary loop of a magnetic resonance apparatus according to the first aspect; exposing the material to an RF magnetic field produced by the primary loop as a result of the current induced in the primary loop according to an RF pulse sequence; receiving an RF output signal generated by the secondary coils; and processing the RF output signal to determine the mass or concentration of the target material.

In some embodiments, the method further includes exposing the material to successive pulse sequences with different frequencies to effectively span a larger frequency range. The frequencies may be obtained from a predetermined list of frequencies.

In some embodiments, the method further includes adjusting the capacitance value of the capacitor unit to vary the series impedance of the primary loop so that the series impedance is close to an optimised reference value. A known relationship between the capacitance value of the capacitor unit and the series impedance of the primary loop may be used to estimate the capacitance value required to set the series impedance to the optimised reference value.

In some embodiments, the method further includes adjusting the impedance of a termination for each auxiliary coil with an auxiliary control unit. The impedance may be adjusted to set the complex impedance of the primary loop to an optimised reference value.

In some embodiments, the method further includes: measuring a temperature of the material; and adjusting at least one of: the frequency of the RF pulse sequence, and the magnitude of the RF output signal; according to the material temperature. The step of adjusting may be conducted according to a known relationship between at least one of: the target resonance frequency, and magnitude of the RF output signal; and the material temperature.

In some embodiments, the method further includes: sequentially measuring the RF output signal at a range of discrete frequencies; and adjusting the frequency of the RF pulse sequence to the frequency corresponding to the maximum RF output signal. In some embodiments, the method further includes: sequentially measuring the RF output signal at a range of discrete frequencies to estimate a magnetic resonance distribution; performing a peak fitting analysis of the estimated magnetic resonance distribution to determine a frequency corresponding to the peak of the estimated magnetic resonance distribution; and adjusting the frequency of the RF pulse sequence to the determined frequency corresponding to the peak of the estimated magnetic resonance distribution.

BRIEF DESCRIPTION OF DRAWINGS

Embodiments are described in further detail below, by way of example, with reference to the accompanying drawings briefly described below.

DETAILED DESCRIPTION

Magnetic resonance (MR) is a powerful analytical technique and is ubiquitous in many fields, such as in fundamental studies of atomic and molecular bonding, the routine laboratory characterisation of materials and medical imaging. The vast majority of applications involve the laboratory use of conventional Nuclear Magnetic Resonance (NMR) for measurements of hydrogen and carbon nuclei to analyse organic compounds, usually in high resolution instruments employing strong applied static magnetic fields (e.g. 5.8-14.1 T). Other less common classes of magnetic resonance include Nuclear Quadrupole Resonance (NQR) and NMR in magnetically ordered materials. These less common classes are applicable to the solid state only, but provide several important measurement advantages. Firstly, in these cases an external static magnetic field need not be applied to define and measure resonances. Secondly, the resonant frequencies are strongly dependent on chemical bonding and crystalline structure and are therefore generally highly specific to a particular target mineral.

In most MR apparatuses, radiofrequency (RF) magnetic fields (normally the near field region of an inductive coil) are applied to materials. In practical terms, the near field region may be defined as the region including both the interior of the inductive sensor and a region surrounding the sensor that extends to a distance equal to a few diameters of the sensor. The RF magnetic fields excite target nuclei within the materials, when applied either in the form of a pulse sequence of discrete pulses or as a continuous wave excitation. The response of the nuclei within the material to the applied RF magnetic fields may be regarded as a time varying magnetisation that generates an associated RF magnetic field. If the RF magnetic field due to the nuclei within the material is within the near-field region of a sensor coil (either the same inductive coil used for excitation, or a different coil), then voltages may be produced at output terminals of the sensor which can then be used for detection of the RF magnetic field associated with the material being analysed. For detection based on Faraday's Law the terminal voltage is proportional to the time rate change of magnetic flux threading an aperture defined by sensor coil. The magnitude of signal voltages generated in the sensor coil may be used to determine the mass of a specific material within the sensing volume. With auxiliary knowledge of the mass loading inside the sensing volume, the concentration of the material may also be determined.

Figure 1:
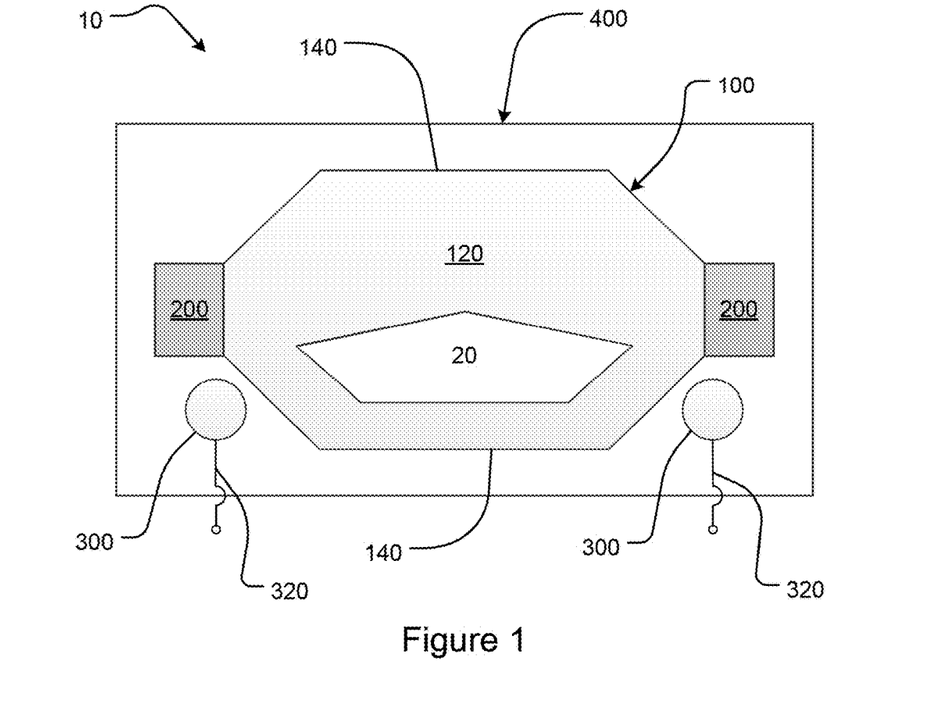
FIG. 1 is a schematic diagram of a magnetic resonance apparatus.

With reference to FIG. 1, a magnetic resonance apparatus 10 is provided for analysing a material 20. The magnetic resonance apparatus 10 includes a primary loop or primary coil 100 (the excitation and sensor loop) which defines an aperture 120 that the material 20 to be analysed can pass through. The primary loop 100 includes at least a pair of electrically conductive segments 140 and a pair of capacitance units 200 corresponding to each pair of electrically conductive segments 140. Each capacitance unit is electrically conductively connected to two adjoining conductive segments in series so that the primary loop 100 forms an electrical circuit for a radio frequency (RF) electrical current.

The primary loop 100 is adapted to have a series resonance frequency suitable for magnetic resonance measurements of the target nuclei. The primary loop 100 conducts the RF electrical current so that it is predominantly in-phase over the entire primary loop. The RF current generates an RF magnetic field suitable for changing the magnetisation of the target nuclei; such as, by resonantly exciting the target nuclei to change the orientation of the net magnetisation of the ensemble of target nuclei. Also, the primary loop 100 is adapted to have an RF signal current excited in the primary loop 100 by precession of the magnetisation of the target nuclei in the material 20 being analysed.

In some embodiments, the predominantly in-phase RF current in some portions of the primary loop 100 may be out of phase with the RF current in another portion of the primary loop 100 by up to 20 degrees. In some embodiments, the predominantly in-phase RF current in some portions of the primary loop 100 may be out of phase with the RF current in another portion of the primary loop 100 by up to 10 degrees.

As appreciated by the person skilled in the art, the resonant absorption and emission of energy by the ensemble of target nuclei may have a frequency distribution. The peak magnetic resonance frequency is defined as the mode of the frequency distribution. The series resonance frequency of the primary loop 100 may be suitable for magnetic resonance measurements of the target nuclei when the series resonance frequency is close to the peak magnetic resonance frequency. Setting the series resonance frequency close to the peak resonance frequency of the target nuclei improves the sensitivity of the magnetic resonance apparatus 10 to small amounts of target nuclei by enabling a greater RF signal current to be excited in the primary loop 100. For example, the series resonance frequency may be set such that the excited RF current is within two standard deviations (of the magnetic resonance frequency distribution of the target nuclei) from the peak magnetic resonance frequency of the target nuclei.

The magnetic resonance apparatus 10 also includes at a pair of secondary coils 300 corresponding to each pair of capacitor units 200 that are electrically conductively isolated from the primary loop 100. Each secondary coil 300 is adapted to receive an RF excitation voltage from an external RF transceiver via an electrical network, and is oriented to be magnetically coupled to the primary loop 100 such that each secondary coil is capable of: exciting RF voltages in the primary loop 100 that are predominantly in-phase with each of the RF voltages excited by the other secondary coils and, when the RF signal current is excited in the primary loop 100 due to a precessing magnetisation of the target nuclei of the material 20 being analysed, having a corresponding RF voltage excited in the secondary coils 300 to produce an RF output signal in the electrical network. The person skilled in the art will appreciate that the RF voltage in the secondary coils 300 can result in a corresponding RF current in the secondary coils 300.

In some embodiments, the predominantly in-phase RF voltage in some portions of the primary loop 100 may be out of phase with the RF voltage in another portion of the primary loop 100 by up to 20 degrees. In some embodiments, the predominantly in-phase RF voltage in some portions of the primary loop 100 may be out of phase with the RF voltage in another portion of the primary loop 100 by up to 10 degrees.

The magnetic resonance apparatus 10 further includes a primary shield 400 encompassing the primary loop 100 and the at least two secondary coils 200 for shielding electromagnetic radiation. The primary shield 400 is adapted to allow the material 20 to pass through the aperture 120 defined by the primary loop 100 unobstructed.

Figure 1A:
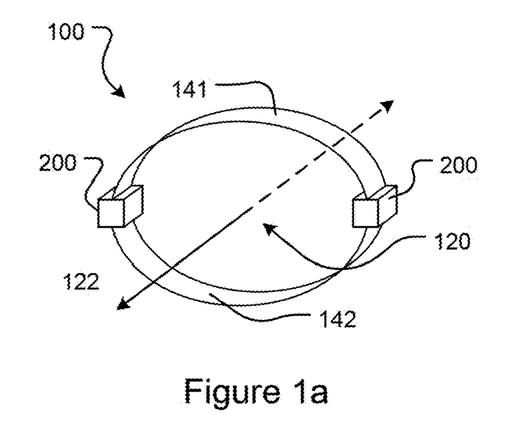
FIG. 1a is a perspective view of a primary loop for some embodiments of the magnetic resonance apparatus shown in FIG. 1.

The primary loop 100 defines a closed current path for oscillating current such as RF current. Referring to FIG. 1a, in some embodiments, the primary loop 100 includes a first arcuate conductive segment 141 electrically connected to a first capacitance unit 201 at one end of the first segment 141 and connected to a second capacitance unit 202 at an opposing end of the first segment 141. The primary loop 100 also includes a second arcuate conductive segment 142 electrically connected to the first capacitance unit 201 at one end of the second segment 142 and connected to the second capacitance unit 202 at an opposing end of the second segment 142. This structure approximates a single turn electrically conducting loop that physically defines the current path. This current path generates an RF magnetic field predominantly along the axis aligned with the normal 122 of the plane that is co-planar with the aperture 120.

The splitting of the primary loop 100 into conductive segments 141, 142 with capacitor units enables the phase of oscillating current in each segment 141, 142 (and therefore the entire primary loop 100) to be more consistent over a large circumference. This advantageously enables material to be analysed over a large sensing volume.

Referring back to FIG. 1, in some embodiments the electrically conductive segments 140 may include bends rather than curves to define an arcuate shape. In preferred embodiments, the electrically conductive segments 140 are shaped such that they can be located close to the material 20 to be analysed. For example, the conductive segments 140 may be shaped so that the primary loop 100 defines an aperture 120 with the shape of a flattened polygon such as a hexagon or octagon. In other embodiments the aperture 120 may have the shape of an ellipse as shown for the arcuate electrically conductive segments 141, 142 in FIG. 1a.

The circumferential length of each of the electrically conductive segments 140 is substantially equal to each other to facilitate the production of the RF electrical currents that are predominantly in-phase over the entire primary loop. For example, the lengths of the electrically conductive segments 140 may deviate by up to 25%. This advantageously allows the capacitance units 200 to be substantially evenly spaced and placed at opposite ends of the primary loop 100. Evenly spacing the capacitance units 200 also allows the voltage between terminals of the capacitance units 200 and nearby structures surrounding the terminals of the capacitors units 200 (terminal voltage) to be reduced.

As shown in FIG. 1a, in some embodiments the conductive segments 140 may be formed from a ribbon of conductive material. The ribbon may be self-supporting or may be mechanically supported by non-conductive material, for example, in the form of a plastic frame. In some preferable embodiments, the plastic frame is weather proof for outdoor applications of the magnetic resonance apparatus 10.

Figure 2:
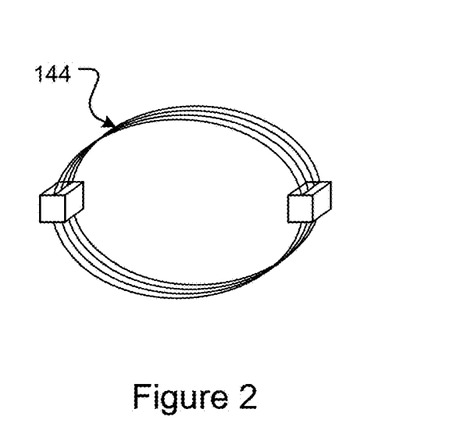
FIG. 2 is a perspective view of an alternative primary loop for some embodiments of the magnetic resonance apparatus shown in FIG. 1.

Referring to FIG. 2, in some other embodiments the conductive segments 140 for the primary loop 100 may comprise a plurality of conductive elements 144 electrically connected to each other in parallel. The conductive elements 144 may, for example, be thin conductive ribbons, arcuate wires or portions of a wire loop.

As the primary loop 100 RF voltage is distributed across at least two capacitance units 200 and at least two primary loop conductive segments 140, the need for designs that require extremely high terminal voltages is mitigated. This advantageously allows more intense RF magnetic fields to be produced without very high terminal voltages.

As shown in FIG. 1, the secondary coils 300 may be adapted to carry an RF current through an electrical connection 320.

Figure 3:
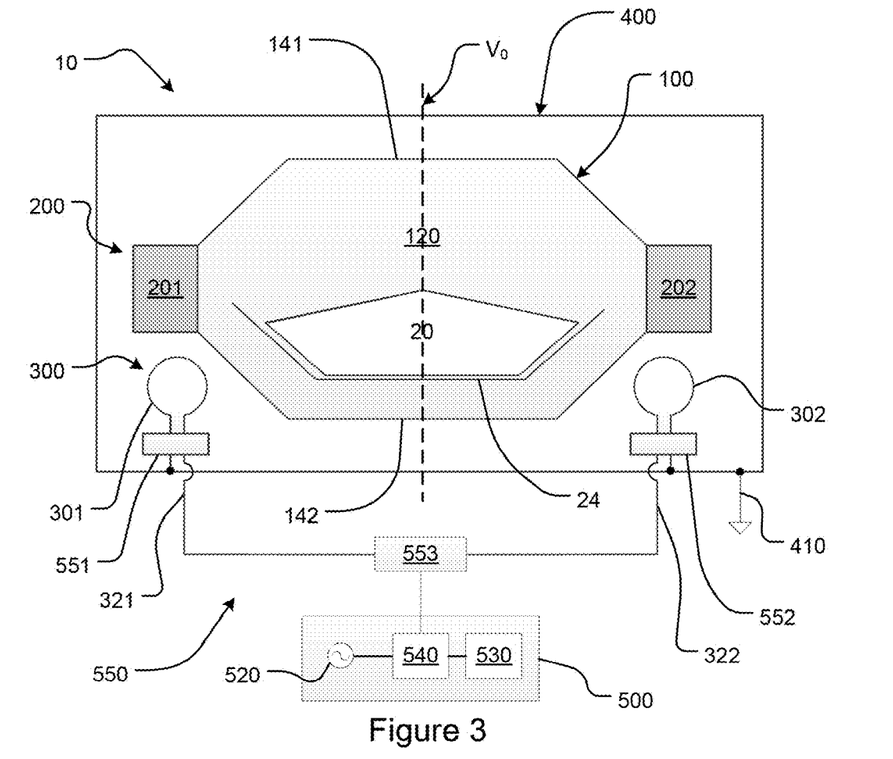
FIG. 3 is a schematic diagram of an embodiment of the magnetic resonance apparatus shown in FIG. 1.

Referring to FIG. 3, in some embodiments, the aperture 120 is adapted to allow a conveyor belt 24 carrying the material 20 being analysed to pass through the aperture. In such embodiments, the arrangement of a primary loop 100 encompasses the conveyor belt 24 carrying the material 20 and ensures that all of the material 20 inside the primary loop is relatively evenly exposed to an RF magnetic field. It also provides a favourable magnetic field polarisation for conveyors with large metal content in the form of long wire metal cores that reinforce the belts of the conveyors and extend along the length of the belts. As the primary loop 100 is oriented such that the RF magnetic fields are approximately aligned in the same direction as the metal cores (at least within the primary loop 100) only a relatively small eddy current is generated on the surface of the cores. If the RF magnetic fields were oriented normal to the length of the cores larger eddy currents would be produced. This would affect the RF magnetic field strength and the field pattern that the material 20 is exposed to.

In the embodiment shown in FIG. 3, the magnetic resonance apparatus includes a pair of capacitance units 201 & 202 that are located on the primary loop 100, thereby creating an electrical circuit for oscillating currents between the adjacent conductive segments 141 & 142 that are between the capacitance units 201 & 202. The positions of the capacitance units 201 & 202 are chosen such that they are located on opposite sides of the primary loop 100.

In the embodiment shown in FIG. 3, the capacitance units 201 & 202 are placed near the side edges of the conveyor belt 24. This also advantageously allows the loop to be constructed in at least two separate pieces, and aids with practical installation of the loop. Each capacitance unit 200 is set with a substantially equal capacitance value to facilitate the production of the RF electrical currents that are predominantly in-phase over the entire primary loop. The common value is chosen such that the primary loop 100 is series resonant at an operating frequency close to the magnetic resonance frequency of the target nuclei. The magnetic resonance frequency may be in the range between 1-200 MHz which is relevant to most ore materials.

Figure 3A:
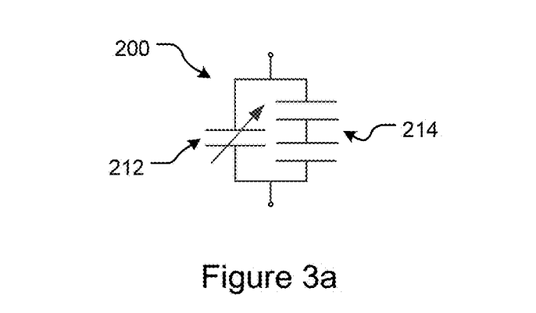
FIG. 3a is a circuit diagram for an embodiment of a capacitance unit.

Referring to FIG. 3a, the capacitance units 200 may be composed of multiple individual capacitors 214 arranged in series or parallel arrangement, and where one or more of the individual capacitors may be a variable (trimmer) capacitor 212.

The primary loop 100 is maintained in an electrically floating state and is electrically conductively isolated from other components of the MR apparatus 10 so as to minimise the effects of a primary loop 100 common mode voltage that may arise from electrostatic coupling with external noise sources. A degree of isolation is achieved by positioning the secondary coils 300 in close proximity to the primary loop 100, as shown in FIGS. 1 & 3. At least one pair of secondary coils 300 is required and the secondary coils 300 may include any one of: a single loop, a single turn coil or a multi-turn coil.

The magnetic coupling between the secondary coils 300 and the primary loop 100 results in RF power transfer to the primary loop 100 without the need to electrically connect the primary loop 100 directly to other nearby structures. The magnetic coupling may be optimised by substantially aligning the axes of the secondary coils 300 with that of the primary loop 100.

In order to generate a predominantly in-phase current component around the primary loop 100, the currents in the secondary coils are arranged so as to induce predominantly in-phase voltage contributions in the primary loop 100 in series. This can be achieved, for example, by selecting similar orientations of the secondary coils 300 with respect to the primary loop 100 such that current in the secondary coils 300 can result in in-phase voltage in the primary loop 100. In practice, small deviations from in-phase primary voltage drive may be tolerated thereby resulting in predominantly in-phase voltage contributions. Both the particular orientation and the network configuration act to make possible the final requirement of predominantly in-phase voltage contributions in the primary loop.

As shown in FIG. 3, a first secondary coil 301 and second secondary coil 302 may be physically located near the respective positions of the capacitor units 201 and 202. The positioning of both the capacitance units 200 and secondary coils 300 as described herein act to reduce spatial inhomogeneity in the magnitude of the current at different points around the primary loop 100.

The voltage distribution over the primary loop 100 and potential differences between points on the primary loop 100 and the surrounding structures, such as the primary shield 400, depends on how the primary loop electrostatically couples to the surrounding structures and in particular how the primary loop 100 electrostatically couples to the secondary coils 300. In some embodiments, the first secondary coil 301 is located on a first side of the primary loop 100 and the second secondary coil 302 is located on a second side of the primary loop 100 such that the first secondary coil 301 and second secondary coil 302 are symmetrically located about the primary loop 100, for example symmetric about a line of zero potential difference line $V_0$ that is formed. The points of intersection between the line $V_0$ and the primary loop 100 have the same potential with respect to the surrounding structures. Therefore there is no electric field along the line $V_0$ joining the points of intersection.

It is advantageous for the line of zero potential difference $V_0$ to be vertically oriented and located over the position where the material 20 to be analysed passes to assist in ensuring that the line of zero potential difference $V_0$ passes through the material 20 being analysed symmetrically, even if the material 20 passing through varies in height. This assists in controlling the voltage distribution in the primary loop 100 as potential differences between different points on the primary loop can act to electrostatically couple with the material 20 which can induce undesirable electrical loadings or losses in the primary loop 100. If the secondary coils 300 were located asymmetrically around the primary loop 100 it is less likely that the zero potential difference line would symmetrically pass through material 20.

As described earlier, the MR apparatus further includes a primary shield 400. The primary shield 400 is electrically conductively isolated from the primary loop 100. The function of the primary shield 400 is to at least partially suppress: emission of electromagnetic radiation by the primary loop 100 into the far-field of the primary loop at the apparatus operating frequency; and the primary loop 100 receiving RF electromagnetic fields emanating from far-field external sources. The primary shield 400 also acts as a second element of a two-element transmission line, the first element being composed of the primary loop 100. The primary shield 400 therefore acts in part to define the impedance between the primary loop 100 and the external environment. In some embodiments, an external electrical connection point 410 on the primary shield 400 may be connected to a locally convenient electrical potential reference point 410 such as a ground potential.

Figure 4:
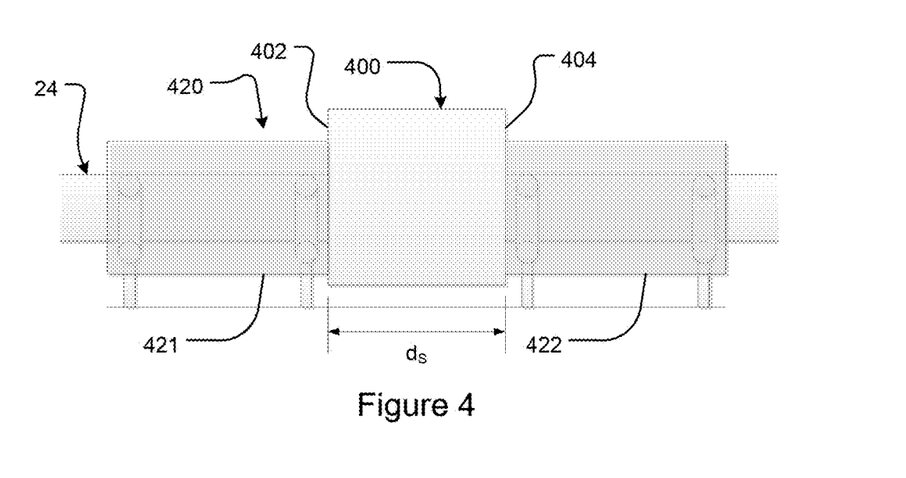
FIG. 4 is a side view of an embodiment of a magnetic resonance apparatus.

As shown in FIG. 4, the primary shield 400 defines at least two openings 402 & 404 at each end of the primary shield 400. The openings 402 and 404 are shaped to be large enough to allow material 20 to pass through the primary shield 400 and primary shield 400 is large enough that primary loop 100 can be located within the primary shield 400. In embodiments where the material 20 is transferred by a conveyor belt 24, the openings 402 & 404 are also shaped to enable the conveyor belt 24 to pass through. The primary shield 400 is extended along a length (ds) between the opening 402 and 404 thereby defining a tunnel, the tunnel shaped to enable the primary loop 100 and secondary coils 200 to be encompassed by the shield 400 and located within the tunnel.

In some embodiments, the primary shield 400 may be, electrically conductively connected to the secondary coils 300. In some embodiments, as shown in FIG. 3, the secondary coils 301, 302 are connected to the primary shield 400 via electrical networks 551, 552 where one terminal of each of the electrical coupling networks 551 and 552 may be connected to the primary shield 400.

Referring back to FIG. 3, the magnetic resonance apparatus is illustrated as previously described but is shown connected to an RF transceiver 500. The RF transceiver 500 may include an RF generator 520, an RF receiver 530, a transmit-receive switch 540 and other suitable electronics to produce an RF excitation voltage in the form of an RF pulse sequence and receive an RF output signal for MR measurements. The MR apparatus 10 is adapted to be connected to an RF transceiver 500. The secondary coils 300 are connected to the RF transceiver 500 via the electrical coupling network 550. The electrical coupling network 550 is configured to transmit RF electrical currents, produced by the RF generator 520 in the transceiver 500, to the secondary coils 300 such that in-phase RF voltages can be produced in the primary loop 100. The electrical coupling network 550 includes the electrical networks 551 and 552 which may be positioned within the primary shield 400. The electrical coupling network 550 also includes a spitter network 553 that connects the RF transceiver to the secondary coils 300 to enable the RF transceiver 500 to evenly supply RF voltages to the secondary coils 300 and allow RF output signals from the secondary coils 300 to be received by the RF transceiver 500. The RF transceiver 500 may then be connected to a data storage or computing device for storing and/or processing the RF output signal received.

The electrical networks 551 and 552 used to provide a coupling to the secondary coils 300 have several functions:

a. The electrical networks 551, 552 may be used to cancel out secondary coil inductance at the operating frequency, leaving only the primary loop reflected impedance as the input impedance for the secondary coil. In some embodiments, the network is a lumped capacitor. Cancelling the secondary inductance advantageously provides a more predictable impedance variation with changes in electrical load parameters.

b. The electrical networks 551, 552 may be used to provide a broadband secondary coil feed. For example, a higher order lumped network can be used to develop wider input bandwidth than would otherwise be the case. Higher input bandwidth is advantageous for transfer function control.

c. The electrical networks 551, 552 may be used to provide a further current phasing condition. There may be some improvements with respect to noise pick up if electrical coupling network 550 is used to provide some anti-phased feeds, and these are re-phased at the secondary coils using networks 551 and 552.

In the embodiment shown in FIG. 3, the magnetic resonance apparatus 10 is adapted to connect to an electrical coupling network 550 that the RF transceiver 500 is connected to. The electrical coupling network 550 is connected to the secondary coils 300 and is configured to simultaneously achieve: correct matching of the RF transceiver 500 to the secondary coils 300 at the operating frequency, and correct phasing of secondary coil currents to produce in-phase voltages in the primary loop 100.

The person skilled in the art will appreciate that there are a variety of secondary coil electrical coupling networks 550, and electrical networks 551 and 552 that can be used to achieve the functions described above. For example, the networks 550, 551 and 552 may take the form of a lumped electrical filter to impose certain phase relationships between input and output voltages. Alternatively, the networks 550, 551 and 552 may be composed of transmission line elements.

The MR apparatus 10 is used to induce a change in the polarisation of the nuclear spin magnetisation in target nuclei in the material 20 within an interaction region defined by the sensing volume encompassed by the primary loop 100. This may then result in an RF precessing magnetisation due to the magnetic resonance of some target nuclei of the material 20 being analysed. This induced change in the nuclear spin magnetisation can be performed by using the RF transceiver 500 to repetitively apply an RF pulse sequence to the secondary coils 300, where the operating frequency is set to a predetermined frequency that is approximately equal to the magnetic resonance frequency of the target nuclei of interest. The person skilled in the art will appreciate that a variety of RF pulse sequences may be used to induce a RF nuclear magnetisation. For example, the Hahn pulse sequence commonly used in magnetic resonance spectroscopy may be used for this purpose. A Carr-Purcell-Meiboom-Gill (CPMG) sequence may also be used to similar effect.

The dynamic RF magnetisation produced by the target nuclei induces an RF electromotive force in the primary loop 100 which generates an RF current in the primary loop 100. RF output signal voltages are consequently generated in the secondary coils 300. The RF output signal voltages at the output of the secondary coil electrical networks 551 and 552 may be received using the RF transceiver 500 and the signal may then be recorded or transmitted to the computing device for further processing. The RF transceiver 500 may include a transmit/receive switch 540 to prevent the RF receiver 530 electronics from being affected by the RF excitation voltages. The RF transceiver 500 may, for example, be configured so that the RF receiver 530 only received RF output signals at a predetermined time after the RF excitation voltages have ended. The RF output signal characteristic for the target nuclei is thereby detected by the magnetic resonance apparatus 10.

The person skilled in the art will appreciate that there are many different methods of configuring the RF transceiver 500 and transmit-receive switch for the purpose of signal detection and subsequent electronic storage. In some embodiments, a separate RF transmitter and RF receiver may be used in place of the RF transceiver 500.

In an exemplary embodiment of the MR apparatus pulsed RF currents at an operating frequency $f_o$ of 18.5 MHz, close to the magnetic resonance frequency of copper-63 nuclei (the target nuclei) in the mineral chalcopyrite, are applied to secondary coils 300. This induces an RF current in the primary loop 100 which then produces an RF magnetic field at the operating frequency in the sensing volume enclosed by the primary loop 100. The primary loop 100 is octagonal in cross section with a 1.5 m width and an inductance L of 1.5 uH. A single pair of capacitor units 200 is positioned at the edges of an ore conveyor. The resistance R of the primary loop is set at 1 ohm, leading to a sensor quality factor $2\pi f_o L/R$ of approximately 180. A Hahn pulse sequence is used to change the polarisation of the nuclear spin magnetisation.

A method of determining the concentration of a specific substance in an analysed material 20 is also provided. Further to detection and electronic storage of the radiofrequency signals with the magnetic resonance apparatus, the RF signals may be analysed to determine the mass of target material per unit length along a conveyor system in the measurement zone of the apparatus. The person skilled the art will appreciate that there are a variety of signal metrics and processing techniques that may be used to determine the mass of target material. For example, where the Hahn pulse sequence is used the detected signal includes a spin echo, the peak magnitude of a generated spin echo may be estimated from the signal and assumed to be linearly proportional to the mass of target material. In addition, the signal may also be normalised by the mass per unit length of all materials on the conveyor system to determine the concentration of the target material. The mass per unit length of all material on the conveyor system in the measurement zone may be obtained, for example, by using a conventional weightometer for conveyors. If the conveyed ore speed is variable, then the conveyed ore speed may also be used in a procedure to determine the material concentration. An example of an equation to calculate the concentration is as follows:

$$C_m = \alpha \langle S \cdot V \langle / \rangle R \rangle.$$

$C_m$ is the average concentration of the target material over a chosen integration time, $\alpha$ is a fixed calibration factor, S, V and R are the instantaneous signal, conveyed ore speed and tonnage rate, respectively, and the angled brackets denote the time average value over the integration time. The person skilled in the art will appreciate that there are a variety of methods available to transmit consecutive computed $C_m$ values to other plant equipment for use in on-line applications. In an example of an application of the method described, the tonnage rate may be 1300 tonnes per hour and an integration time of 20 seconds may be used.

Secondary Shields

Industrial environments may produce large amounts of spurious electromagnetic noise from various sources, such as motors. Noise from external sources may be attenuated by placement of at least one secondary shield 420 adjacent to the primary shield 400. At least one secondary shield 420 is configured such that material 20 can pass through each of the secondary shield 420, the primary shield 400 and the aperture 120 of the primary loop 100. In the embodiment shown in FIG. 4, a conveyor belt 24 is used to transfer material 20 through the primary shield 400 and the primary loop aperture 120 within the primary shield (not shown). There is a first secondary shield 421 encompassing the conveyor belt at one end of the primary shield 400 and a second secondary shield 422 at the opposite end of the primary shield 400. The secondary shields 420 acts as waveguides below cut-off at particular frequencies to reduce coupling of the primary loop 100 and the secondary coils 300 to external noise sources. The secondary shields' dimensions are such that they act as waveguides below cut-off at the operating frequency to further shield the sensing volume defined by the primary loop 100 from external noise signals that occur at the operating frequency. The secondary shields 420 also serve the purpose of attenuating the electromagnetic fields generated by the primary loop 100 in regions adjacent to the primary shield 400. The person skilled in the art will appreciate that a number of different waveguide cross-sectional shapes may be used to similar effect to reduce coupling to external sources. In some embodiments, the secondary shields are in electrical contact with the primary shield.

Noise Signal Compensation

Figure 5:
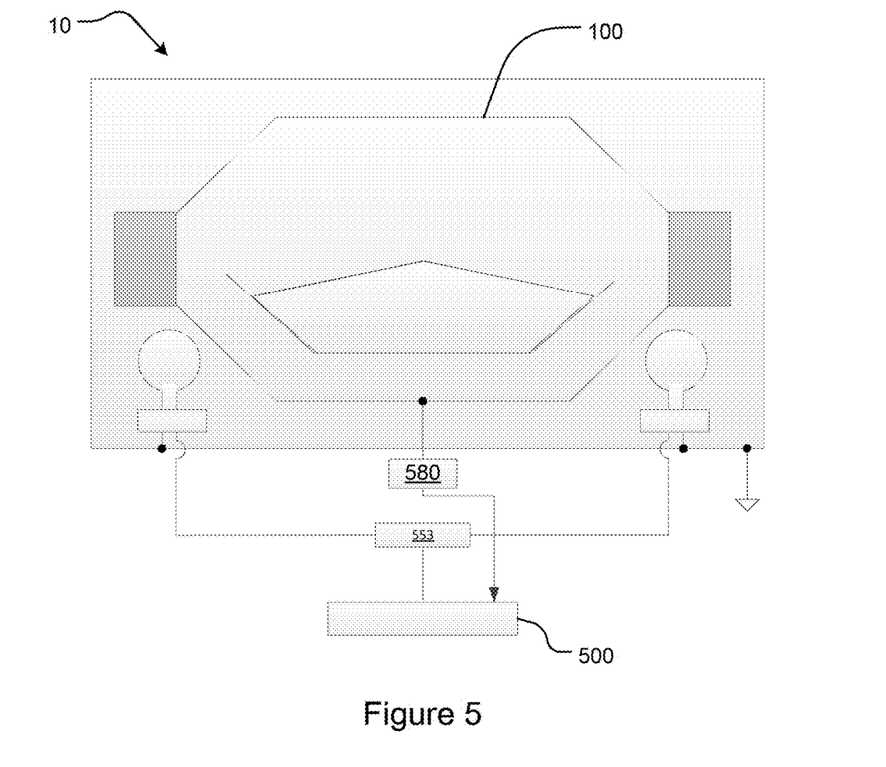
FIG. 5 is a schematic diagram of an embodiment of the magnetic resonance apparatus shown in FIG. 3.

Electrostatic coupling between the primary loop 100 and surrounding electromagnetic noise sources may generate a primary loop 100 common mode voltage. Because of unavoidable imperfect isolation between primary loop 100 and secondary coils 300 a component of the primary loop 100 common mode voltage may couple to the secondary coils 300 and provide a spurious noise signal at the RF transceiver 500. In some embodiments, at least one of the conductive segments 140 is adapted to enable the voltage at a location approximately midway along the conductive segment 140 to be sampled. As shown in FIG. 5, an electrical connection is made to segment 142 at the midway point between the ends of the segment 142 (midway between the adjoining capacitance units 200). This connection may be provided as electrical terminals or access points, such that the voltage at the selected point can be sampled. The electrical connection is connected to the RF transceiver by an electrical sampling circuit 580 such that the sampling circuit 580 delivers a suitable voltage to the RF transceiver 500 equal in magnitude but opposite in phase to the spurious noise voltage. As the sampled voltage is associated with spurious noise voltage the effect of the spurious noise is reduced and thereby at least partially compensated for. It is preferable that a high input impedance is presented by the electrical sampling circuit 580 to minimise current flow from the primary loop 100 into the electrical sampling circuit 580.

Floating Electrode Shields

Figure 6:
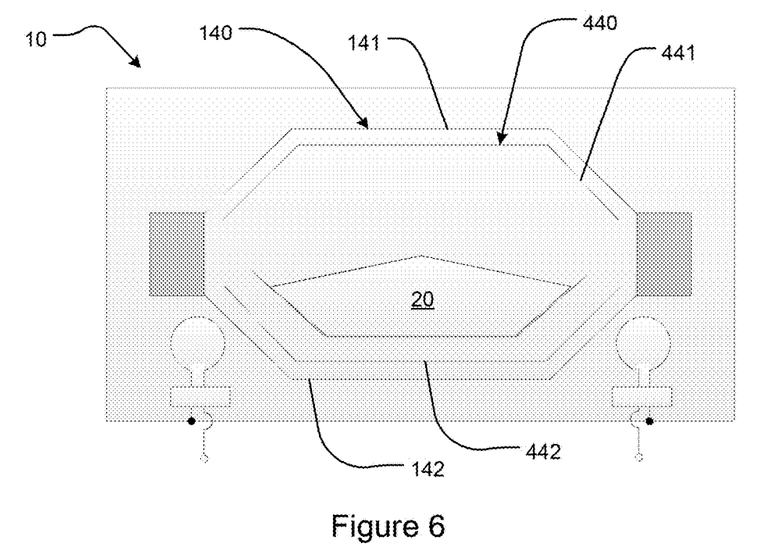
FIG. 6 is a schematic diagram of an embodiment of the magnetic resonance apparatus shown in FIG. 3.

In some embodiments, electrostatic coupling between the primary loop 100 and surrounding noise sources may be further reduced by introducing at least one floating electrode shield 440 between the primary loop 100 and the material 20 being analysed as shown in FIG. 6, where the number of electrode shields 440 equals the number of conductive segments 140. The floating electrode shields 440 are electrically conductively isolated. In particular, the floating electrode shields 440 are isolated from the primary loop 100 and the primary shield 400. The floating electrode shields 440 produce an equipotential surface for electric field lines that terminate on its surface and that are generated by spurious noise sources. The floating electrode shields 440 span an area between each capacitance unit and overlay each conductive segment 140 of the primary loop 100, in order to provide a symmetrised voltage distribution over the primary loop 100. For example, as shown in FIG. 6, a first floating electrode shield 441 overlays the first conductive segment 141 and the second floating electrode shield 442 overlays the second conductive segment 142.

It is preferable that the electrodes are made of conducting substance having thickness much less than the substance's electromagnetic skin depth at the operating frequency. As this skin depth varies with operating frequency, the thickness may be different if different operating frequencies are used. Alternatively, the thickness may be determined based on the range of operating frequencies of most interest.

In embodiments where the conductive segments 140 include a flat surface such as a ribbon, it is preferable that the floating electrode shields 440 are shaped to conform to a surface parallel to the surface of the corresponding conductive segment 140. The floating electrode shields 440 are thereby shaped and arranged to reduce the electrical loss they impart.

Pilot Coils

Variations in ore burden on the conveyor system may be encountered over time. These variations may vary the complex series impedance of the primary loop 100 and induce shifts in the phase relationship and magnitude ratios of the primary loop 100 current and primary loop 100 voltage. In turn, these shifts may cause variations in the transfer function between induced primary loop 100 voltage and voltages generated at the RF transceiver 500. This can inhibit accurate quantitative measurements of materials.

Figure 7:
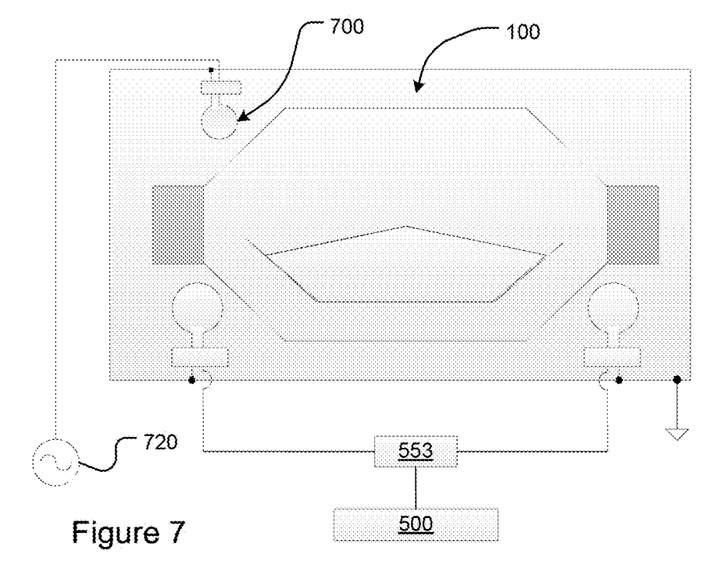
FIG. 7 is a schematic diagram of an embodiment of the magnetic resonance apparatus shown in FIG. 3.

In some embodiments, the MR apparatus 10 includes a pilot coil 700 magnetically coupled predominantly to the primary loop 100 (as shown in FIG. 7). The pilot coil 700 is adapted to be connected to a RF source 720 that can produce a pulsed RF current in the pilot coil 700 at predetermined frequencies near the magnetic resonance frequency of the target nuclei, during periods when the primary loop 100 is not used for producing an RF magnetic field or for signal detection. The RF current in the pilot coil produces an RF magnetic field and the pilot coil 700 currents acts to induce a voltage at the RF transceiver 500 via the magnetic coupling to the primary loop 100. The resulting voltage magnitude and phase at the RF transceiver 500 may be compared to a reference magnitude and phase. Differences in magnitude and phase may be used to determine a correction that can be applied to the RF output signal to account for changes in the transfer function. Only small pilot coil currents may be needed to determine the transfer function in the described manner and the location of the pilot coil 700 within the primary shield 400 is not particularly important.

Auxiliary Coils

The operating frequency may need to be adjusted to values outside the circuit bandwidth defined by the series resonance of the primary loop 100, such that power transfer to the primary loop 100 from the RF transceiver 500 would become non-optimal. This may be due, for example, to transmitter-load mismatch and this can inhibit accurate quantitative measurements of materials.

Figure 8:
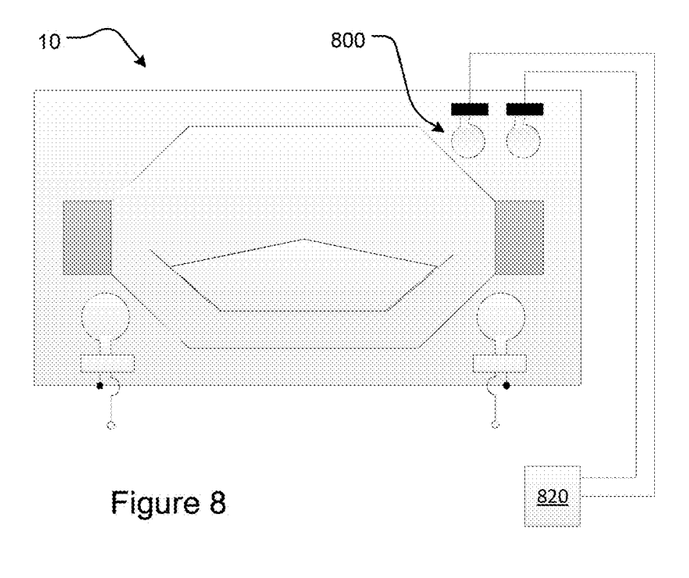
FIG. 8 is a schematic diagram of an embodiment of the magnetic resonance apparatus shown in FIG. 3.

The mismatch may be remedied by altering the complex ratio between current and loop voltage in the primary loop 100 (the complex impedance) and setting it to a predetermined value such as an optimised reference value. In some embodiments, one or more auxiliary coils 800 may be magnetically coupled to the primary loop 100 as shown in FIG. 8. The auxiliary coils 800 include a termination that may consist of a resistor but may also be an electrical network including at least one resistor and at least one other component such as a capacitor. The terminated auxiliary coils 800 affect the complex impedance of the MR apparatus 10 and, unlike the pilot coil 700, the auxiliary coils 800 are passive components in that no RF power is supplied to the auxiliary coils 800. The terminating impedance of any of the auxiliary coils 800 may be modified to alter the complex ratio of the primary loop 100 voltage and the primary loop 100 current, such that the power coupling to the primary loop 100 is optimised. In some embodiments, the auxiliary coils are controlled by an auxiliary control unit 820. The modification of the auxiliary coil termination may be achieved by electronic means within the auxiliary control unit 820. The person skilled in the art will appreciate that the complex ratio of primary loop 100 voltage and primary loop 100 current may be determined through the measurement of circuit node voltages and currents. The required termination modification to set the correct complex ratio may be determined by comparing the measured ratio to the required ratio, and computing the required change in terminating impedance based on a known relationship between the terminating impedance and complex ratio.

The control of the complex ratio of primary loop 100 voltage and current may also be achieved by varying the capacitance of the capacitance unit 200, where the required change in capacitance may be deduced through similar means of comparison of the measured complex ratio to the required complex ratio, using a known relationship between capacitor value and the complex ratio. In some embodiments, the capacitance of the capacitance unit 200 is varied through mechanical alteration of components within the capacitor unit 200.

Frequency Hopping

The RF frequencies of the magnetic fields produced by the primary loop 100 have a certain bandwidth depending on the pulse sequence applied. However, the spectral width of magnetic resonance frequencies of target nuclei in the material may be sufficiently wide to preclude efficient excitation of the entire spectral width. The range of frequencies the material is exposed to may be increased by altering the operating frequency of successively applied pulse sequences so as to effectively span a larger frequency range around a predetermined target frequency. The target frequency may, for example, be the expected magnetic resonance frequency of peak response for the target nuclei in the material of interest. By using operating frequencies that span a larger frequency range, a larger fraction of the spectral width of the target nuclei in the material can be excited and a larger MR signal can be detected which improves sensitivity of the MR method.

The altered operating frequencies may be pre-determined in a list of different operating frequencies with respect to a predetermined target frequency. For example, if the magnetic resonance frequency of the target nuclei is $f_T$, then a predetermined list of frequencies $f_O'$ may be defined by:

$$f_O' = [f_T - 2f_S, f_T - f_S, f_T, f_T + f_S, f_T + 2f_S]$$

where in this example, $f_S$ is a fixed frequency step and where the number of elements N in the list in this example is 5. Other values for N may be used. The list of N frequencies may be accessed in a cyclic manner to repetitively apply each operating frequency in the list. The frequency steps between successive elements in the list need not be fixed, nor monotonically increasing or decreasing.

The RF excitation pulses at each frequency have a spectral width spanning a range of frequencies. The fixed frequency step $f_S$ may be smaller than the spectral width of the RF magnetic field applied at the target frequency to ensure sufficient overlap in the frequencies covered by the altered frequency list. The use of the frequency list results in the excitation of a broader range of magnetic resonance frequencies than would otherwise be possible.

Exemplary Embodiments

Figure 9:
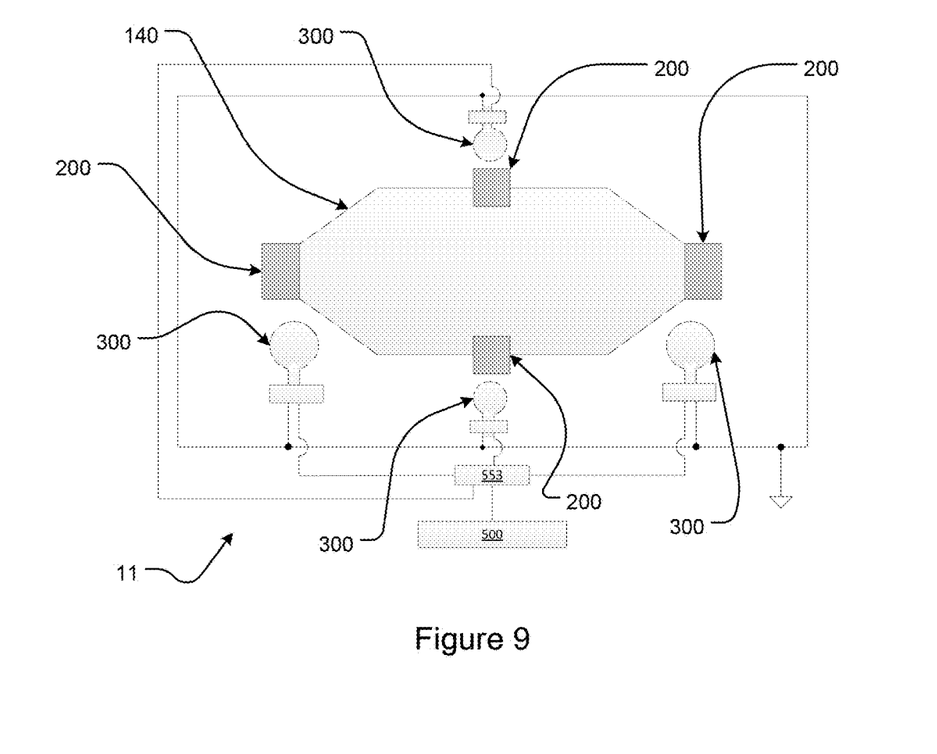
FIG. 9 is a schematic diagram of an embodiment of a magnetic resonance apparatus.

With reference to FIG. 9, in some embodiments, a MR apparatus 11 includes more than two conductive segments 140, capacitance units 200 and secondary coils 300. The conductive segments 140 may be paired and the capacitance units 200 may be grouped in pairs. With reference to FIG. 9, four conductive segments 140, capacitance units 200 and secondary coils 300 are shown. The capacitor units 200 are connected to the ends of the conductive segments 140, such that all the capacitance units 200 are approximately equally spaced around the primary loop 100. The secondary coils 300 are placed near the capacitance units 200.

Figure 10:
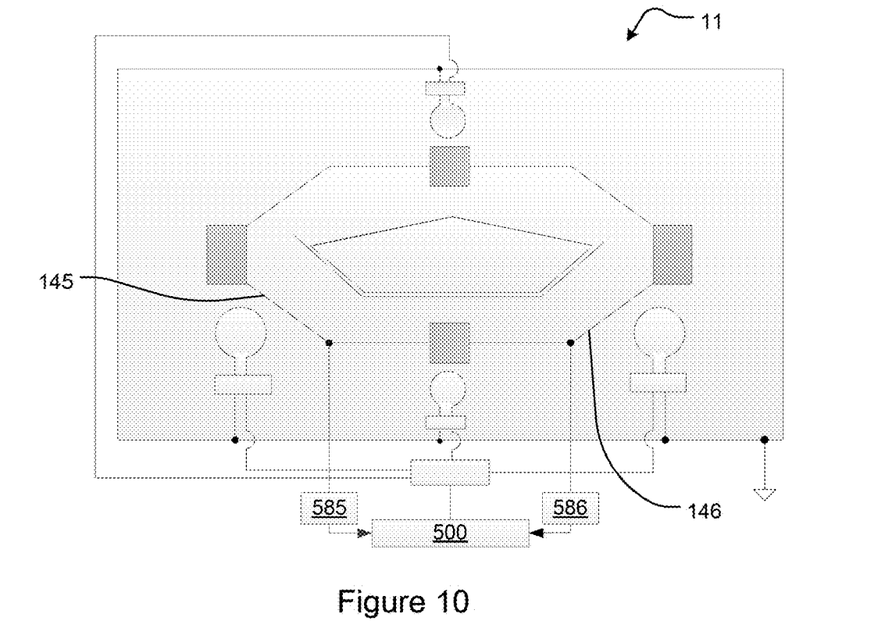
FIG. 10 is a schematic diagram of an embodiment of the magnetic resonance apparatus shown in FIG. 9.

FIG. 10 shows an embodiment of the MR apparatus 11 of FIG. 9 wherein conductive segments 145 and 146 each have an electrical connection to them at the midway point between the ends of the segments. The electrical connection to conductive segment 145 is connected to a first electrical sampling circuit 585 and the electrical connection to conductive segment 146 is connected to a second electrical sampling circuit 586 which each deliver a suitable voltage to the RF transceiver 500 in order for the RF transceiver to compensate for spurious electrical noise.

Figure 11:
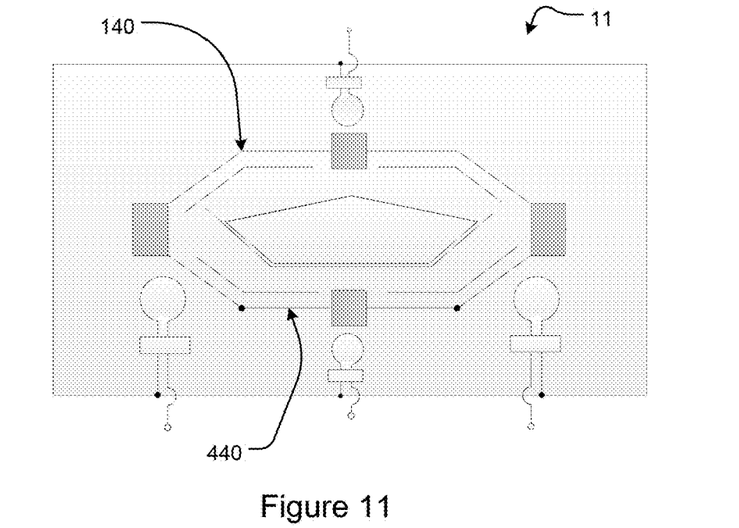
FIG. 11 is a schematic diagram of an embodiment of the magnetic resonance apparatus shown in FIG. 9.

With respect to FIG. 12, an embodiment of the magnetic resonance apparatus 11 is shown with floating electrode shields 440. Four corresponding floating electrodes shields 440 are provided for each of the four conductive segments 140 to act as equipotential surfaces.

In some exemplary applications, the material under investigation is an ore and the ore may be conveyed through an "ore transfer zone" comprising either a chute or vertical transfer station, where all the ore is conveyed through the aperture 120 of the primary loop 100 under the action of gravity. In some instances a chute may need to be partially modified to reduce electromagnetic coupling with the primary loop 100 current. The person skilled in the art will appreciate that there are a number of ways to modify a chute for this purpose.

The magnetic resonance frequency of a target nuclei in the material being analysed may vary according to the target material temperature. The temperature of the material may be measured using known methods. The temperature measurement may then be used to adjust the target frequency so as to align with the predicted magnetic resonance frequency and thereby compensate for the effect of temperature on the resonance frequency. This may be done according to a known relationship between the target resonance frequency of the target nuclei and the material temperature.

In some embodiments, variations in material temperature may be allowed for by sequentially measuring the RF output signal at discrete frequencies. For example, the RF output signal may be measured over a range of frequencies around the expected spectral distribution of the magnetic resonance frequencies for the target nuclei. The RF output signal may be, for example, recorded at multiple discrete frequencies, where the frequency is hopped through the magnetic resonance spectrum to estimate or approximate the magnetic resonance spectral distribution. The frequency corresponding to the peak of the magnetic resonance spectral distribution may be estimated by the frequency in the hopped sequence that corresponds to the maximum magnitude of RF output signal. The RF target frequency may then be adjusted to the frequency at which the peak RF output signal occurs.

In other embodiments, the approximate frequency at which the peak of the magnetic resonance distribution occurs may be deduced by performing a peak fitting analysis across the RF output signals (measured at a range of discrete frequencies) that are used to estimate the magnetic resonance distribution. The RF target frequency may then be adjusted to the so determined frequency corresponding to the peak of the estimated magnetic resonance distribution. An example of a fitting analysis is a Gaussian peak fitting analysis.

In some embodiments, the magnitude of the RF output signal from the secondary coils 300 may also be adjusted to compensate for effects from the material temperature. This adjustment may be conducted according to a known relationship between the magnitude of the RF output signal and the material temperature. For example, the known relationship may be the Boltzmann factor associated with magnetic resonance detection.

Any one of the described embodiments may incorporate features from any one of the previously described embodiments. For example, any one of the described embodiments may include: conductive segments 140 with electrical access points and sampling circuits 580, floating electrodes 140, pilot coils 700 or auxiliary coils 800 and respective auxiliary control units 820.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A magnetic resonance apparatus for analysing a material, the magnetic resonance apparatus including:
a primary loop defining an aperture that the material being analysed can pass through, the primary loop including:
at least one pair of electrically conductive segments; and
a pair of capacitance units corresponding to each pair of electrically conductive segments, each capacitance unit conductively connected to two adjoining conductive segments in series so that the primary loop forms a circuit for a radio frequency (RF) current;
wherein the primary loop is adapted to:
have a series resonance frequency suitable for magnetic resonance measurements of the target nuclei,
conduct the RF electrical current so that the RF electrical current is predominantly in-phase over the entire primary loop,
conduct the RF current to generate an RF magnetic field suitable for changing the magnetisation of the target nuclei, and
have an RF signal current excited in the primary loop by precession of the magnetisation of the target nuclei;
the magnetic resonance apparatus further including:
a pair of secondary coils corresponding to each pair of capacitor units, electrically conductively isolated from the primary loop, wherein each secondary coil is adapted to receive an RF excitation voltage from an RF transceiver via an electrical network, and is oriented to be magnetically coupled to the primary loop such that each secondary coil is capable of:
exciting RF voltages in the primary loop that are predominantly in-phase with each of the RF voltages excited by the other secondary coils; and
when the RF signal current is excited in the primary loop, having a corresponding RF current excited in the secondary coil to produce an RF output signal in the electrical network; and
a primary shield encompassing the primary loop and secondary coils for shielding electromagnetic radiation, the primary shield adapted to allow the material to pass through the aperture defined by the primary loop unobstructed.

2. The magnetic resonance apparatus of claim 1, wherein the primary loop is a single turn loop.

3. The magnetic resonance apparatus of claim 1, wherein the electrically conductive segments include either: a single conductive ribbon; or a plurality of conductive elements electrically connected to each other in parallel.

4. The magnetic resonance apparatus of claim 1, wherein the capacitance of each capacitor unit is substantially equal to each other to facilitate the production of the RF electrical currents that are predominantly in-phase over the entire primary loop.

5. The magnetic resonance apparatus of claim 1, wherein the capacitance of each capacitor unit is capable of being varied.

6. The magnetic resonance apparatus of claim 1, wherein the length of each of the electrically conductive segments is substantially equal to each other to facilitate the production of the RF electrical currents that are predominantly in-phase over the entire primary loop.

7. The magnetic resonance apparatus of claim 1, wherein the primary shield is connected to a reference voltage and one side of the secondary coil electrical network port is electrically conductively connected to the primary shield.

8. The magnetic resonance apparatus of claim 1, wherein the aperture is adapted to allow either a conveyor belt or a chute carrying the material being analysed to pass through.

9. The magnetic resonance apparatus of claim 1, further including at least one secondary shield located adjacent the primary shield, the secondary shield reducing the effect of spurious electromagnetic fields on the primary loop.

10. The magnetic resonance apparatus of claim 9, wherein the secondary shield is a waveguide configured such that the material can pass through the secondary shield.

11. The magnetic resonance apparatus according to claim 1, further including an RF transceiver, wherein the RF transceiver includes an RF generator and is configured to produce the RF excitation voltages received by the electrical networks of at least two secondary coils.

12. The magnetic resonance apparatus of claim 11, further including an electrical coupling network, the electrical coupling network connected to the two or more secondary coils and the RF transceiver, wherein the electrical coupling network is configured to transmit RF electrical currents, produced by the RF transceiver, to the secondary coils such that predominantly in-phase RF excitation voltages can be produced in the primary loop.

13. The magnetic resonance apparatus of claim 11, further including a sampling circuit, wherein at least one of the conductive segments is adapted to enable a voltage at a location midway along the at least one conductive segment to be sampled, and the voltage sampled from the conductive segment is converted to a suitable voltage by the sampling circuit and input into the RF transceiver to at least partially compensate for electromagnetic noise.

14. The magnetic resonance apparatus according to claim 1, further including two or more electrically floating electrode shields, each floating electrode shield corresponding to one conductive segment and located such that the corresponding conductive segment is located between the floating electrode shield and the primary shield.

15. The magnetic resonance apparatus according to claim 1, further including one or more pilot coils magnetically coupled to the primary loop and adapted to produce an RF magnetic field at predetermined frequencies.

16. The magnetic resonance apparatus according to claim 1, further including one or more auxiliary coils magnetically coupled to the primary loop, the one or more auxiliary coils each having a termination, wherein the auxiliary coil alters the complex series impedance of the primary loop.

17. The magnetic resonance apparatus of claim 16, wherein the impedance of the termination for each auxiliary coil is adjustable with an auxiliary control unit.

18. A magnetic resonance system for analysing a material, the system including:
   the magnetic resonance apparatus for analysing the material according to claim 1; and
   a radio frequency (RF) transceiver including an RF generator and a transmit-receive switch, the RF transceiver is connected to the secondary coils and adapted to:
   apply an RF pulse sequence to the secondary coils with at least an operating frequency set to a predetermined frequency capable of inducing change in the magnetisation in an ensemble of target nuclei in the material, and
   receive an RF output signal generated by the secondary coils in cooperation with the transmit-receive switch.

19. A method of determining the mass of a target material in an ore, the method including:
   passing a material through an aperture of a primary loop of a magnetic resonance apparatus according to claim 1;
   exposing the material to an RF magnetic field produced by the primary loop as a result of the current induced in the primary loop according to an RF pulse sequence;
   receiving an RF output signal generated by the secondary coils; and
   processing the RF output signal to determine the mass or concentration of the target material.

20. The method of claim 19, further including exposing the material to successive pulse sequences with different frequencies to effectively span a larger frequency range.

* * * * *